United States Patent [19]
Franklin et al.

[11] Patent Number: 5,215,094
[45] Date of Patent: Jun. 1, 1993

[54] ULTRASONIC FLOW VELOCITY IMAGING SYSTEMS WITH VELOCITY IMAGE PRESISTENCE

[75] Inventors: Donn D. Franklin; Jeffry E. Powers, both of Lake Stevens, Wash.

[73] Assignee: Advanced Technology Laboratories, Inc., Bothell, Wash.

[21] Appl. No.: 799,667

[22] Filed: Nov. 21, 1991

Related U.S. Application Data

[63] Continuation of Ser. No. 613,200, Nov. 14, 1990, abandoned.

[51] Int. Cl.$^5$ ............................................. A61B 8/06
[52] U.S. Cl. .......................... 128/661.08; 128/662.02
[58] Field of Search ................... 128/661.07, 661.08, 128/661.09, 662.01, 662.02

[56] References Cited

U.S. PATENT DOCUMENTS

| | | | |
|---|---|---|---|
| 4,403,184 | 9/1983 | Witt et al. | 128/661.07 |
| 4,509,525 | 4/1985 | Seo | 128/661.09 |
| 4,794,932 | 1/1989 | Baba | 128/661.09 |
| 4,800,891 | 1/1989 | Kim | 128/661.09 |
| 4,850,366 | 7/1989 | Ito et al. | 128/661.08 |
| 4,961,427 | 10/1990 | Namekawa et al. | 128/661.09 |
| 5,123,417 | 6/1992 | Walker et al. | 128/661.09 |

Primary Examiner—Kyle L. Howell
Assistant Examiner—George Manuel
Attorney, Agent, or Firm—W. Brinton Yorks, Jr.

[57] ABSTRACT

An ultrasonic diagnostic imaging system is described which enhances the presentation of flow velocity images through asymmetric persistence of visually displayed changes in fluid velocity. Preferably the asymmetric persistence employs a shorter (i.e., faster) time constant for increases in fluid velocity and a longer (i.e., slower) time constant for decreases in fluid velocity. In a preferred embodiment of the present invention, increases in fluid velocity are displayed at their rate of occurrence, and decreases in fluid velocity are displayed with a longer, user-selectable time constant. In the preferred embodiment the persistence enhancement is determined as a function of displayed image frame rate so that the persistence time constant remains fixed as a function of time despite user changes affecting the frame rate.

13 Claims, 6 Drawing Sheets

FIG-2
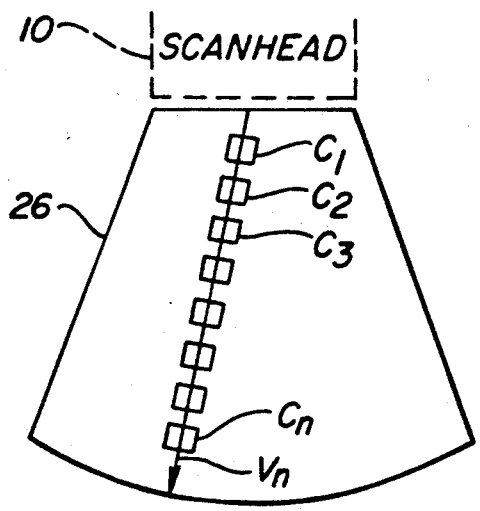
FIG-3
| | $P_1$ | | $P_2$ | | $P_3$ | | $P_4$ | |
|---|---|---|---|---|---|---|---|---|
| $C_1$ | $I_{10}$ | $Q_{10}$ | $I_{11}$ | $Q_{11}$ | $I_{12}$ | $Q_{12}$ | $I_{13}$ | $Q_{13}$ |
| $C_2$ | $I_{20}$ | $Q_{20}$ | $I_{21}$ | $Q_{21}$ | $I_{22}$ | $Q_{22}$ | $I_{23}$ | $Q_{23}$ |
| $C_3$ | $I_{30}$ | $Q_{30}$ | $I_{31}$ | $Q_{31}$ | $I_{32}$ | $Q_{32}$ | $I_{33}$ | $Q_{33}$ |
| | | | | | | | | |
| | | | | | | | | |
| | | | | | | | | |
| | | | | | | | | |
| $C_n$ | $I_{n0}$ | $Q_{n0}$ | $I_{n1}$ | $Q_{n1}$ | $I_{n2}$ | $Q_{n2}$ | $I_{n3}$ | $Q_{n3}$ |
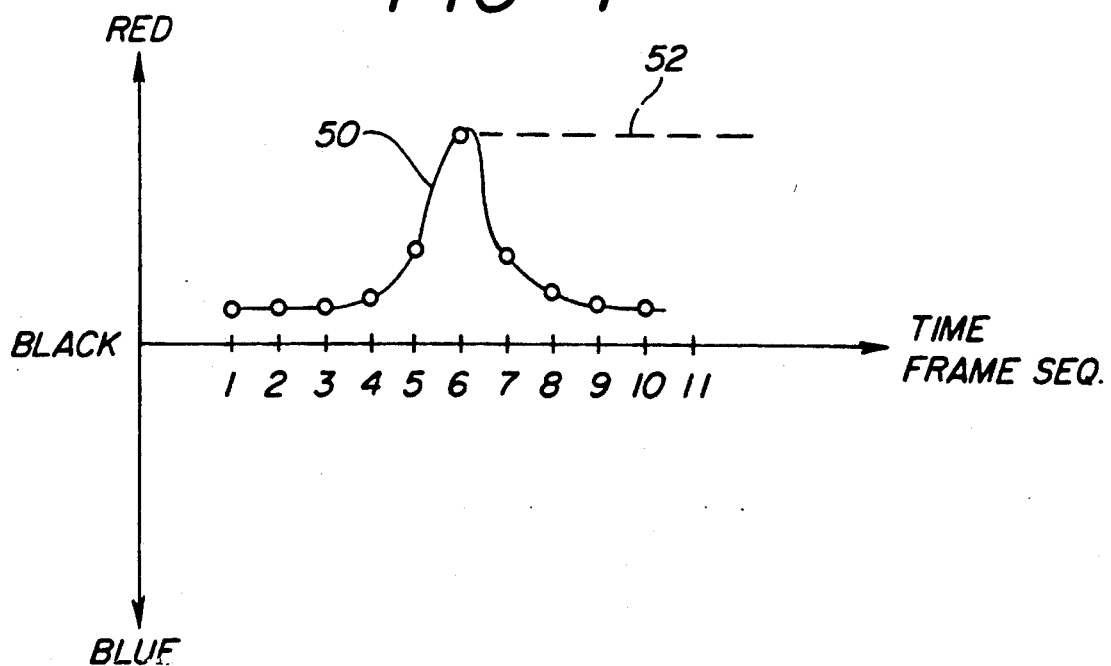
FIG-4

ULTRASONIC FLOW VELOCITY IMAGING SYSTEMS WITH VELOCITY IMAGE PRESISTENCE

This is a continuation of application Ser. No. 613,200, filed Nov. 14, 1990 now abandoned.

This invention relates to ultrasonic diagnostic systems which through Doppler interrogation measure and display the velocity of moving fluids within the body of a medical patient and, in particular, to the enhancement of such fluid velocity displays by means of asymmetric persistence.

Ultrasonic diagnostic imaging systems are presently available which make use of both pulse echo techniques and Doppler techniques to simultaneously image tissue structure within the body and fluids which are moving within that structure. The fluids are not represented structurally, but as a function of their flow velocities. A preferred technique for representing fluid velocity, such as the velocity of flowing blood, is a color presentation commonly known as color flow imaging. In color flow imaging, blood flow in a first direction relative to the ultrasonic scanhead is displayed in a first color, such as red, with hue or intensity indicating velocity. Correspondingly, blood flow in a second, opposing direction relative to the scanhead is displayed as a varying hue or intensity of a second color such as blue. Color flow imaging has been shown to be clinically viable such as by enabling a clinician to detect irregularities in the circulatory system of the body through the color representation of subtle changes in blood flow velocity and/or direction.

For certain applications of color flow imaging the clinician is trying to discern fluid flow conditions which are at the limits of diagnostic system capabilities. These applications include those where the abnormal flow characteristic which is being explored occurs only momentarily or in a very precise location, such as a small jet of blood flow in a much larger volume of blood. In such an application the clinician may be interested in the momentary, peak velocity of the jet. A known technique for acquiring this briefly recurring information is color capture, by which the color image or map detects and holds peak velocity values. In color capture the color map at first changes rapidly over the field of view as initial velocity data is acquired. The map then changes ever more slowly as the velocity values of the map are incrementally updated toward the color values of peak velocity. At the end of the process the image appears frozen with the peak velocity values captured in the color map. Color capture performs well for its intended purpose, but lost in the process is the primary virture of the ultrasound modality, the ability to sense the dynamics of the body through real-time imaging. It would be desirable to employ color flow imaging in a manner which clearly depicts peak values of flow velocity without sacrifice of the dynamics of real-time imaging.

In accordance with the principles of the present invention, an ultrasonic diagnostic imaging system is described which enhances the presentation of flow velocity through asymmetric persistence of changes in fluid velocity. Preferably the asymmetric persistence employs a shorter (i.e., faster) time constant for increases in fluid velocity and a longer (i.e., slower) time constant for decreases in fluid velocity. In a preferred embodiment of the present invention, increases in fluid velocity are displayed at their rate of occurrence, and decreases in fluid velocity are displayed with a longer, user-selectable time constant. In the preferred embodiment the persistence enhancement is determined as a function of displayed image frame rate so that the persistence time constant remains fixed as a function of time despite user changes affecting the frame rate.

In the drawings:

FIG. 2 illustrates an area being interrogated for Doppler flow information;

FIG. 3 illustrates an array of data values resulting from Doppler interrogation along an ultrasonic vector;

FIG. 4 illustrates flow velocity data points occurring during a momentary change in fluid flow velocity;

Figure 1:
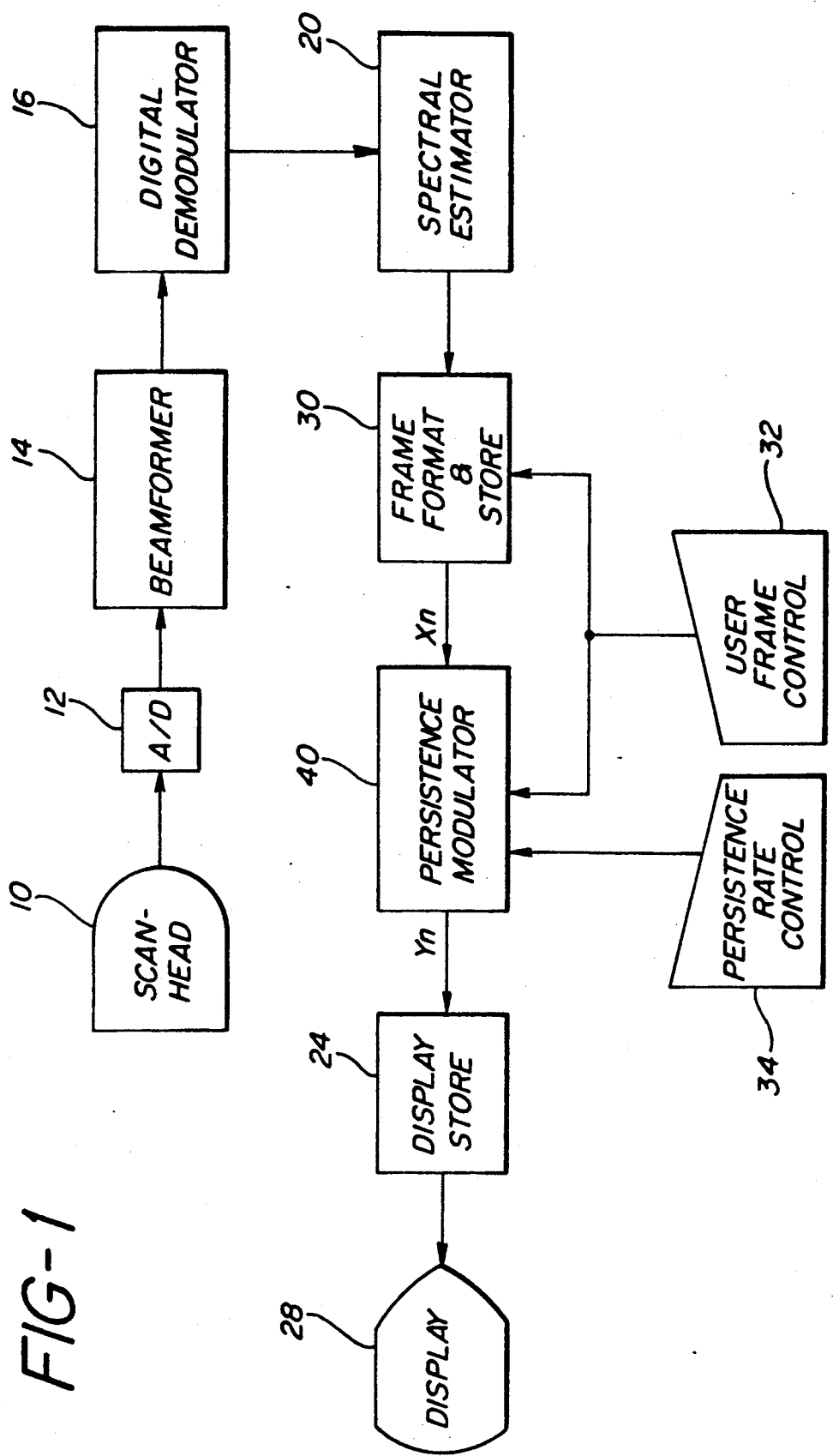
FIG. 1 illustrates in block diagram form a flow velocity imaging system constructed in accordance with the principles of the present invention.

Referring first to FIG. 1, a flow velocity imaging system constructed in accordance with the principles of the present invention is shown in block diagram form. A scanhead 10 containing one or more piezoelectric transducer elements transmits ultrasonic waves into the body of a patient and receives ultrasonic echoes returned by the tissue and fluid structures of the body. The returning echoes are converted to electrical signals by the transducer(s) and the signals are then digitized by an analog to digital converter 12. A plurality of such digital signal samples are combined in a beamformer 14 to form coherent ultrasonic information signals which are coupled to a digital demodulator 16. The fluid flow velocity information contained in the ultrasonic information signals is encoded as phase shifts of the returning echo signals in relation to a reference signal. Accordingly the demodulation process involves a translation of the ultrasonic information signals to an intermediate frequency range and the resolution of the phase information into two components, an in-phase (I) component and a quadrature (Q) component. The output of the digital demodulator 16 thus is a stream of corresponding I and Q phase information signals containing information as to the velocity of fluids and tissue in the patient's body.

The I and Q phase information signals are applied to the input of a spectral estimator 20, which determines the fluid velocities as represented by the Doppler content of the signals. The velocity information signals produced by the spectral estimator 20 are then applied to a frame format and store module 30 which stores the velocity information in correspondence with its location in an image. In a preferred embodiment, the velocity information is stored locationally as a function of the position in the scanned area of the body at which the measurement was taken.

In accordance with the principles of the present invention successive frames of color flow information are applied to a persistence modulator 40, which monitors and detects changes in velocity occurring over time at respective image locations. The persistence modulator receives inputs from a user operated persistence rate control 34 and a user frame control 32, the latter also being coupled to the frame format and store module. The persistence modulator enhances the information to be displayed by recalculating the displayed values in accordance with inputs from the user control. Specifically, data values representing increasing velocity are displayed in the manner in which they are received, while data values representing decreasing velocity are enhanced so as to increase the persistence of the higher velocity values in the image. The enhanced frames of color flow image data are stored in image frame format in a display store 24, then transmitted to an image display 28 for viewing the flow velocity image information.

FIG. 2 depicts the manner in which Doppler data may be acquired to form a color flow image. The scanhead 10 sequentially transmits ultrasonic pulses in a plurality of vector directions over the scanned area 26 of the patient's body. One of these vector directions is indicated by arrow $V_n$ in FIG. 2. As echoes are returned from tissue and fluids along direction $V_n$, signal samples are taken from echoes returning from sequential positions along the vector. These positions are referred to herein as range cells, some of which are labelled C1, C2, C3, ... $C_n$ in the FIGURE. The signal samples are processed by the beamformer 14 and converted by the digital demodulator 16 to I and Q quadrature signal samples.

This sequence of pulse transmission and echo reception is repeated a number of times along vector direction $V_n$. The transmitted pulses of four of these sequences are labelled $P_1$, $P_2$, $P_3$, and $P_4$ in the chart of FIG. 3. The I,Q echo samples taken in response to each of these pulse transmissions are shown below each pulse in FIG. 3. Each horizontal row of I,Q samples in FIG. 3 thus represents signal samples taken at a particular range cell location $C_1$ ... $C_n$, but at different points in time. An array of data of the form illustrated in FIG. 3 is operated upon by the spectral estimator 20, whereby each horizontal row of I,Q samples is used to determine a velocity value at its particular cell location for one image frame. Once a velocity value has been determined for each range cell in the image frame, the image frame of velocity value data is locationally stored in the frame format and store module 30 for subsequent processing and display. The entire process is then repeated, and the spectral estimator 20 acquires new I,Q data values for determination of new velocity values for the next image frame.

FIG. 4 illustrates the velocity changes that may take place at a particular range cell location over a sequence of image frames when fluid velocity suddenly increases and decreases at that location in the body. The ordinate axis of FIG. 4 represents the range of color-encoded velocity in a typical color flow map. At the center of the range is black, the color that is displayed in the absence of flow (zero velocity). Toward the upper extreme of the range is red, indicating increasing velocity in a first direction. Toward the other extreme of the range is blue representing increasing velocity in the other direction. The abscissa of FIG. 4 represents the passage of time, and the numbers below the abscissa indicate discrete frames of flow velocity values. The curve 50 connects the changing values of velocity (small circles) recorded for the particular range cell location from one frame to the next. FIG. 4 shows that, over a sequence of ten successive frames, the fluid velocity at the range cell location increases from frames one through six, peaks around frame six, then decreases from frame six through frame ten. At a moderate frame rate, such as thirty frames per second, this velocity change would last only one-third of a second. The peak value of frame six would be barely perceptible at this frame rate.

The color capture technique would successively store and display the values of frames one through six during the velocity change of FIG. 4. Once the velocity began to decline following frame six, the peak value of frame six would be retained in the color map and displayed, as indicated by the dashed line 52. The user would then see a stationary color map with the color of the peak velocity of frame six captured and stored at the particular range cell location.

Figure 5:
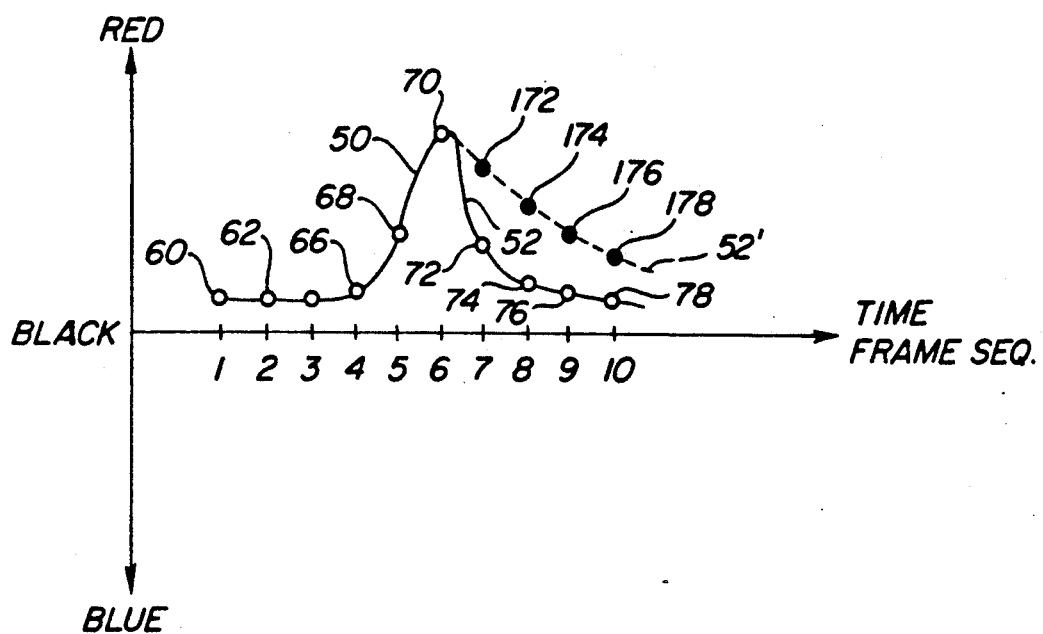
FIG. 5 illustrates the velocity data points of FIG. 4 as enhanced by asymmetric persistence in accordance with the principles of the present invention.

FIG. 5 illustrates how the velocity changes and peak value of FIG. 4 may be enhanced through persistence in accordance with the principles of the present invention. The persistence modulator 40 of FIG. 1 receives the velocity values contained in successive image frames for the range cells where fluid flow is being measured. As the modulator receives the velocity value of a new frame for a particular range cell location, the new velocity value is designated $x_n$ and the value produced by the modulator at the time of the previous frame is designated $y_{n-1}$, where n represents frame sequence. In the example of FIG. 5, the velocity value indicated by circle 60 is received in a first frame and the value indicated by circle 62 is received in a succeeding frame. When the value at 62 is received, it is designated $x_n$ and the value produced by the modulator at the time of the preceding frame is designated $y_{n-1}$. As succeeding values are received, e.g., 66 and 68, the process is repeated; the value previously produced by the persistence modulator is designated $y_{n-1}$ and the newly received value is designated as $x_n$.

Upon receipt of each new $x_n$ value, the modulator performs a comparison of $x_n$ and $y_{n-1}$. If the new value $x_n$ is of greater magnitude than the $y_{n-1}$ value, then the output value $y_n$ of the modulator is equal to $x_n$. Thus, at the time of receipt of frame number 5 in FIG. 5, when $x_n$ has a magnitude as indicated at 68 and $y_{n-1}$ has a magnitude as indicated at 66, the displayed output value $y_n$ is the greater $x_n$ value at 68.

This process continues in the example of FIG. 5 until the time of receipt of frame number 7, when $y_{n-1}$ has a magnitude as indicated at 70 and $x_n$ has a magnitude as indicated at 72. Now the result of the comparison shows that $x_n$ is of lesser magnitude than $y_{n-1}$. With this result the output $y_n$ of the modulator is calculated as a weighted average of the $x_n$ and $y_{n-1}$ values. The $y_n$ value produced at the time of frame number 7 is indicated by the solid circle 172. In FIG. 5 the illustrated weighting is approximately ⅔ of $y_{n-1}$ and ⅓ of $x_n$.

At the time of occurrence of the next frame number 8, $x_n$ is as indicated at 74 and $y_{n-1}$ is the previously calculated $y_n$ value indicated at 172. Again the result of the comparison is that $x_n$ is less than $y_{n-1}$, and a weighted average value is calculated for $y_n$ as indicated at 174. In the example of FIG. 5, weighted average values for $y_n$ would obtain as shown by the solid circles for the balance of the frames through frame number 10.

This modulation technique may be viewed several ways. The transfer function of the persistence modulator 40 may be expressed mathematically as If $x_n > y_{n-1}$, then $y_n = x_n$;

If $x_n \leq y_{n-1}$, then $y_n = (1-k)x_n + ky_{n-1}$,  (1)

where the weighting factor k is greater than zero and less than one.

Another view of the technique is to note that the dashed curve 52' connecting the calculated values 70-178 in FIG. 5 has a longer time constant than the solid curve 52 connecting the original velocity values 70-78. The appearance of these curves is as though the curve of decreasing velocities 52 was processed by a lowpass filter, whereas the curve 50 of increasing velocities was not. This is the asymmetric result of an embodiment of the present invention, in which increases in velocity are processed to exhibit a shorter time constant than are decreases in velocity. In the particular example, increases in velocity from values 60 through 70 are processed to retain their original time constant, whereas velocity value decreases following 70 are processed to exhibit a longer time constant than their original time constant. The effect in the displayed image is that, instead of a momentary, perhaps undetectable, appearance of the peak value 70, the maximal velocity attained appears to persist as the decrease in velocity is given a slower rate of decline. Unlike the image freeze of the color capture technique, the inventive technique continues to process velocity changes which visually vary in real time, thus maintaining the dynamic effect of real time imaging.

In accordance with a further aspect of the present invention, the time constant of the persistence effect is user-selectable. Referring to Table 1, each vertical column shows the appropriate value of k to be used in the weighting expression (1) to achieve a low, medium, or high persistence effect. The relative magnitudes of the k values of each column show that, for a low persistence effect, the previous frame value $y_{n-1}$ is given relatively lesser weight than is the new frame value $x_n$, and for a high persistence effect the $y_{n-1}$ values is given relatively greater weight in the calculation. In FIG. 1 the persistence rate control 34 is adjusted by the user to select the appropriate k value for the desired persistence effect.

Figure 6:
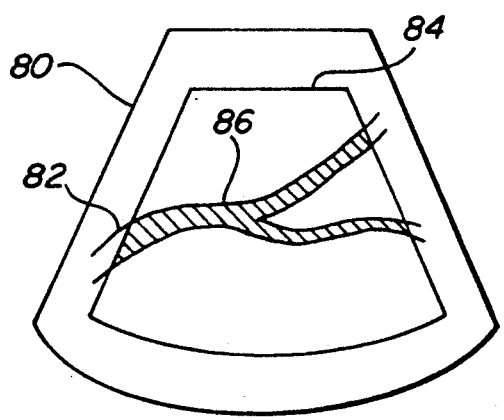
FIGS. 6 and 7 illustrate color flow images with differing color flow windows and frame rates.
Figure 7:
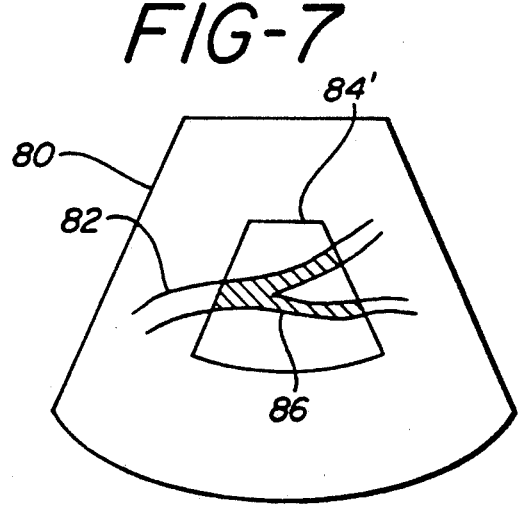

FIGS. 6 and 7 illustrate a further aspect of the present invention, which is a consequence of "windowing" the velocity information in a color flow image. In each of these figures, the area outlined at 80 contains the two dimensional image plane of the body which is being structurally imaged. In the example shown, the structure being imaged is a blood vessel 82. Within this image plane is a user adjustable window 84 or 84', within which the velocities of flowing blood 86 are displayed in color. Because the velocity information is determined as a result of Doppler information acquired over time and the required processing is complex and time consuming, the rate at which new frames of color flow information are computed and displayed can decline significantly when flow velocities over a large area are being interrogated. The frame rate can change for other user-selected operating conditions, such as ensemble length change (the number of $P_n$ pulses per vector line), changes in interrogation depth, etc. In the examples of FIGS. 6 and 7, the frame rate of color flow window 84 would typically be less than that of the smaller color flow window 84' since a much larger number of range cell locations must be interrogated and velocities computed before the full window 84 of color flow information is assembled for display. The lesser number of range cells of window 84' would take less time to interrogate for computation of the needed color flow information. In a constructed embodiment of the present invention, the frame control 32 by which the user varies the window size is a trackball mounted on the imaging system, which can be turned to adjust the window height, width, or both the height and width. As the user adjusts the size of the color flow window with the trackball, the imaging system automatically adjusts the frame rate correspondingly so that the user is continually benefitting from the highest frame rate which may be used for the selected window size.

Figure 8:
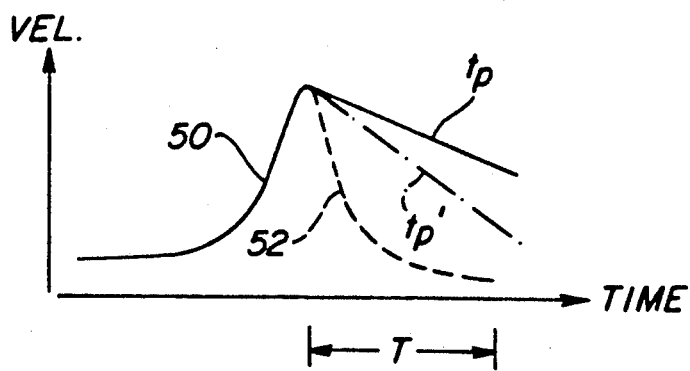
FIGS. 8 and 9 are graphical representations of the effect of frame rate variation on persistence enhancement and employing frame rate equalization in accordance with the principles of the present invention.

The effect of variation in the frame rate during persistence enhancement is that, since the persistence effect operates on sequences of frames, a change in frame rate will change the visually perceived time constant of the persistence effect. As the window size is changed the rate of persistence will also change, and a persistence time constant which the user selected before adjustment of the window would be altered and lost. By way of illustration, FIG. 8 shows an increase and decrease in velocity occurring over time which, without the persistence effect, would change in correspondence with curves 50,52. During the period T of velocity decline, the decrease in velocity is enhanced to exhibit persistence as indicated by line $t_p$. If the frame rate of display is increased, the persistence effect will be diminished as indicated by the broken line $t_p'$. This change in visual perception of the persistence effect can have a deleterious effect on the results of a diagnosis being performed on the image information.

In accordance with a further aspect of the present invention, the weighted averages for the persistence effect are determined as a function of the frame rate, making the persistence effect time constant immune to window and hence frame rate changes. The persistence modulator 40 of FIG. 1 contains a table of weighting factor values such as that shown in Table 1. Across the top of Table 1 is the frame rate, which in this example ranges from 5 frames per second to 50 frames per second. Below each frame rate is a k weighting factor value to be used for each of the three degrees of persistence at the given frame rate. These k values are determined by the expression $$k = e^{-1/[(FR)(t_p)]},$$

where FR is the frame rate and $t_p$ is the persistence time constant. The k values of Table 1 were determined by maintaining the time constant $t_p$ fixed for each horizontal row and calculating k as a function of the frame rate. As the Table shows, as the frame rate increases the weight k given previous frame values $y_{n-1}$ increases and the weight (1−k) given new frame values $x_n$ correspondingly decreases.

Figure 9:
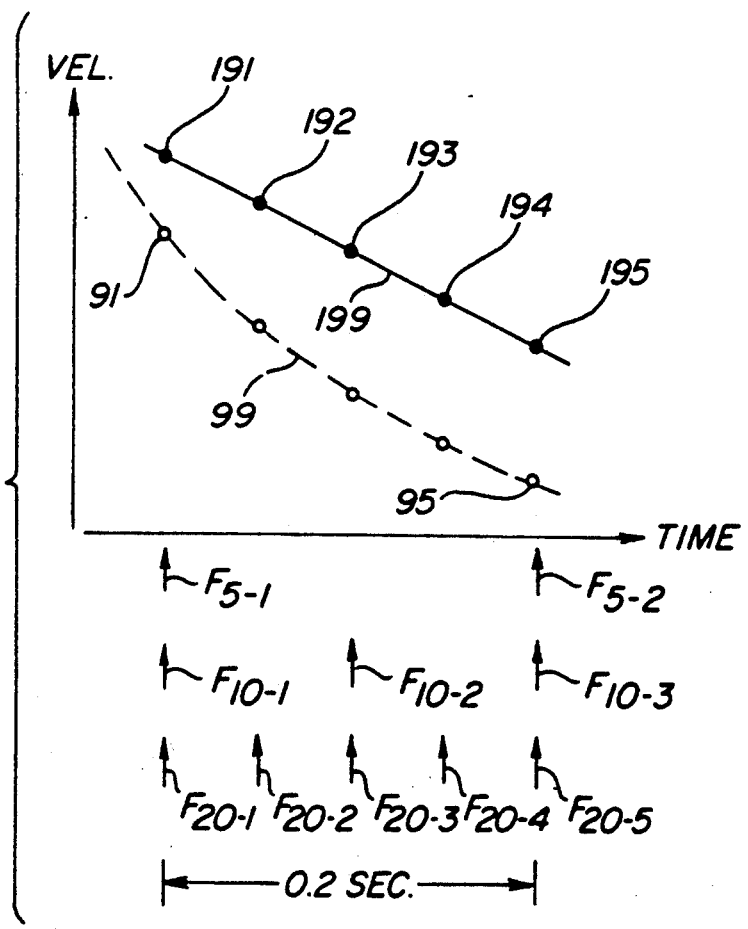

The effect of this variation in weighting factors on the persistence effect in the presence of frame variation may be understood by referring to FIG. 9. This figure shows a curve 99 of declining velocity values 91-95 which is to be enhanced as shown by calculated velocity values 191-195 connected by line 199. The time interval between points 91 and 95 is 0.2 seconds, and the display of visual persistence should follow line 199 over the 0.2 second interval regardless of the frame rate. If velocity values are displayed at a rate of five frames per second, the persistence modulator receives velocity values at the consecutive frame times indicated by arrows $F_{5-1}$ and $F_{5-2}$. At the time of frame $F_{5-2}$ $x_n$ has a value indicated by point 95 and $y_{n-1}$ has a value indicated by point 191. The calculated value produced by expression (1) is as shown by point 195.

If the frame rate is increased to ten frames per second for the same velocity information, velocity values are produced at the consecutive frame times indicated by arrows $F_{10-1}$, $F_{10-2}$, and $F_{10-3}$. At the time of frame $F_{10-3}$ $x_n$ again has a value indicated by point 95, but $y_{n-1}$ now has the value indicated by point 193 at the time of the previous frame $F_{10-2}$. Since the same calculated value at 195 must be obtained, it is apparent that the weighting of $x_n$ and $y_{n-1}$ must change to more greatly weight the value at point 193 in relation to the weight given point 95. The data of Table 1 shows this to be the case, with k increasing and (1−k) decreasing for increasing frame rates. Additionally, a ten frame per second rate of display will result in the display of intermediate velocity value 193 at the time of frame $F_{10-2}$.

FIG. 9 shows the same result occurring for a frame rate of twenty, in which case the value at frame $F_{20-5}$ point 195 is to be obtained using $x_n$ as indicated at point 95 and $y_{n-1}$ as indicated at point 194 of the preceding frame $F_{20-4}$. Display values 19114 195 are produced at each of frame times $F_{20-1}$ through $F_{20-5}$ at the twenty frame per second rate.

Thus it is seen from these examples that, by using weighting factors which are functionally related to the frame rate, the persistence effect calculated and displayed will appear identical to the viewer, regardless of any change of the velocity display window and consequent change of the image frame rate.

Figure 10:
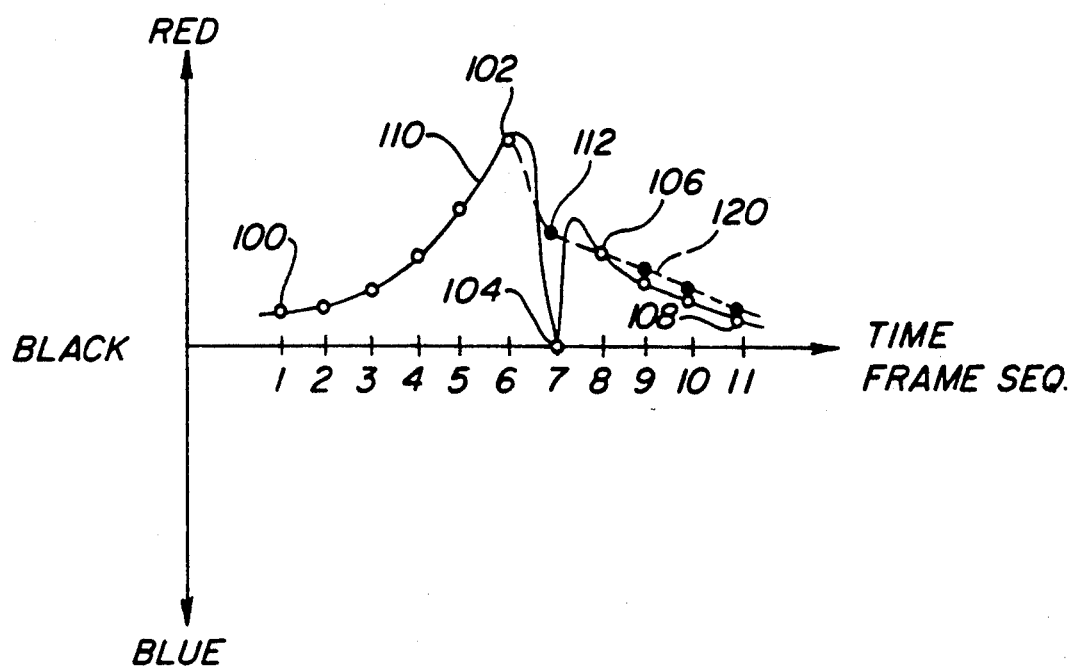
FIGS. 10 and 11 illustrate the dropout filtering characteristic of the flow velocity persistence enhancement of the present invention.

During the collection of color flow information through Doppler interrogation of the body, it is possible for returning ultrasonic information to become lost through random scattering effects and other factors. The occasional loss of signal information in one frame of color flow velocities can result in momentary signal dropout in the displayed color flow information. This condition is illustrated by the frame to frame velocity values depicted by the open circles 100–108 in FIG. 10, which are connected by the solid line 110. FIG. 10 shows the velocity values (and corresponding color) at a particular range cell increasing over time to a peak value 102 at frame number 6. But in frame number 7 there is a sudden dropout to the black level as shown at 104. However, a gradual decline in velocity resumes with frame number 8, and continues through the value 108 in frame number 11. When color flow information of this form is displayed, it will be contaminated with a black, specular effect when the signal dropout occurs with the display of frame number 7.

In accordance with yet a further aspect of the present invention, the persistence modulator of the present invention will reduce the deleterious effects of signal dropout by calculating velocity values for display which smooth over the dropout condition. Moreover, this benefit is not just asymmetrically effective for signal dropout during conditions of velocity value decline, but also operates to smooth over dropout conditions during conditions of increasing velocity. In the example of FIG. 10, at the time of the signal dropout $x_n$ in expression (1) is equal to the value of 104 and $y_{n-1}$ is equal to the value of 102. calculation of the mathematical expression using a weighting factor k=0.5 yields a calculated display value $y_n$ as shown at 112 for frame number 7. When the signal information resumes with value 106 in frame number 8, the comparison of $x_n$ with $y_{n-1}$ results in the value 106 being used for the displayed value $y_n$ in frame number 8. Following frame number 8 the velocity values continue to decline, and calculated, weighted values are used for display as described above. Thus, the persistence modulator of the present invention smoothes over the dropout condition by displaying the values connected by dashed line 120 during the interval between frame number 6 and frame number 11.

Figure 11:
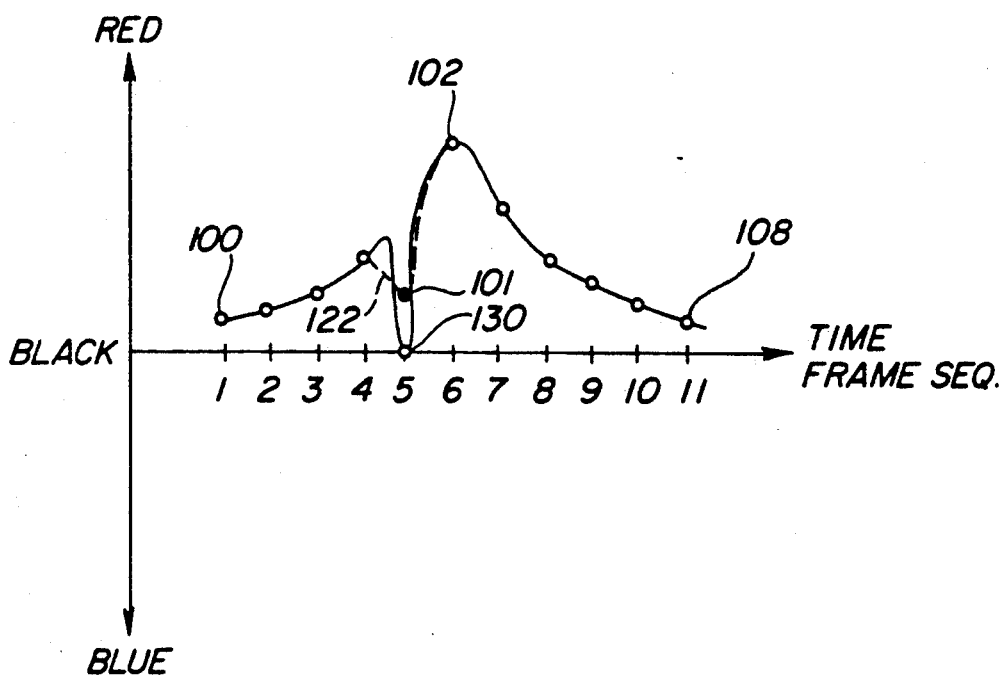

FIG. 11 shows the condition that obtains when the signal dropout occurs during an increase in velocity values. (The effects of the persistence modulator are not shown during the frame number 6 through frame number 11 interval of FIG. 11.) This figure shows that a signal dropout occurs in frame number 5, as indicated by the value 130. The sudden drop in value from frame number 4 to frame number 5 is detected by the comparison of $x_n$ with $y_{n-1}$, resulting in a calculated value 101 being used for display value $y_n$ in frame number 5. Thereafter the increased value 102 is displayed for subsequent frame number 6. Thus it is seen that the unwanted effects of signal dropout are ameliorated during conditions of increasing velocity as a further benefit of the use of a persistence modulator of the present invention.

It may be appreciated that, consistent with the principles of the present invention, the velocity values of more than two frames may be used to compute the weighted values for display. For instance, a weighting expression of the form $Ay_{n-1}+Bx_n+Cy_{n+1}$ could be used to determine the calculated values yn for display. It should also be noted that the present drawings illustrate velocity increases and decreases only in the red direction. The same benefits of the present invention are obtained for velocity increases and decreases in the blue direction, in which case the velocity transitions and persistence effects of the present drawings would appear in mirror image form.

TABLE 1

| Frame Rate | 5 | 10 | 15 | 20 | 25 | 30 | 35 | 40 | 45 | 50 |
| --- | --- | --- | --- | --- | --- | --- | --- | --- | --- | --- |
| Low (0.2) | .368 | .607 | .717 | .779 | .819 | .846 | .867 | .882 | .895 | .905 |
| Med. (0.4) | .607 | .779 | .846 | .882 | .905 | .920 | .931 | .939 | .946 | .951 |
| Hi (0.6) | .717 | .846 | .895 | .920 | .936 | .946 | .953 | .959 | .964 | .967 |

What is claimed is:

1. An ultrasonic diagnostic imaging system for imaging conditions of fluid flow within a body comprising:
   scanhead means for acquiring echo information from structure within the body, including Doppler information signals from fluid moving relative to said scanhead means;
   means responsive to said Doppler information signals for producing fluid velocity signals as a function of location within the body, including a plurality of time sequential, locationally related fluid velocity signals having values depicting an increase in velocity to a maximum velocity value and a decay from said maximum velocity value;
   image processing means responsive to said echo information and said locationally related fluid velocity signals for producing a sequence of images of structure within the body in substantially real time, said image processing means including fluid flow display means responsive to said locationally related fluid velocity signals having values depicting an increase in velocity for displaying fluid velocity increases in said sequence of images in substantially real time, said fluid flow display means being further responsive to said locationally related fluid velocity signals having values depicting a decay from said maximum velocity value for displaying fluid velocity decreases in said sequence of images at a rate which is slower than real time; and means, responsive to said sequence of images produced by said image processing means, for displaying decreases in fluid velocity with a visually extended time of decay.

2. The ultrasonic diagnostic imaging system of claim 1, wherein successive ones of said fluid velocity signals are subject to exhibiting declining velocity values, and wherein said fluid velocity signal producing means includes means for altering the values of ones of said fluid velocity signals depicting a decay from said maximum velocity value.

3. The ultrasonic diagnostic imaging system of claim 2, wherein said altering means operates to increase the magnitude of ones of said fluid velocity signals depicting a decay from said maximum velocity value while leaving unaltered the values of successive fluid velocity signals which depict an increase in velocity.

4. The ultrasonic diagnostic imaging system of claim 3, wherein said display means displays fluid velocity information at a variable rate, and wherein the magnitude of alteration of successive ones of said fluid velocity signals performed by said altering means is functionally related to said display rate.

5. An ultrasonic diagnostic imaging system for imaging conditions of fluid flow within the body comprising:
means for acquiring echo information from structure within the body, including Doppler information signals from fluid moving relative to said acquiring means;
means responsive to said Doppler information signals for producing a sequence of fluid velocity signals as a function of location within the body, wherein successive fluid velocity signals related to a given location indicate increases toward a peak velocity value or decreases in fluid velocity from said peak velocity value at said location occurring over time;
fluid velocity signal alteration means, responsive to successive fluid velocity signal which indicate decreases in fluid velocity, for altering said signals indicating decreases in fluid velocity to lengthen the apparent time of fluid velocity decay from said peak velocity value indicated by the display of successive fluid velocity signals of decreasing fluid velocity values; and
means, responsive to signals produced by said fluid velocity signal alteration means, for displaying fluid velocity with lengthened times of decay from peak velocity values.

6. The ultrasonic diagnostic imaging system of claim 5, wherein successive ones of said fluid velocity signals produced by said Doppler information signal processing means in relation to a common location indicate increases or decreases in fluid velocity in real time at said common location; and wherein said fluid velocity signal alteration means includes means for producing successive fluid velocity signals during periods of fluid velocity increase which indicate rate of fluid velocity increase in real time.

7. The ultrasonic diagnostic imaging system of claim 6, wherein said displaying means comprises means for sequentially displaying a sequence of fluid velocity signals at a rate which causes increases in fluid velocity to visually correspond to actual rate of occurrence, and decreases in fluid velocity to visually correspond to a rate of decline at a time constant increased in relation to actual rate of occurrence.

8. The ultrasonic diagnostic imaging system of claim 5, wherein said displaying means comprises means for sequentially displaying frames of fluid velocity information at a variable frame rate, and wherein said fluid velocity signal alteration means alters said signals indicating decreases in fluid velocity by amounts which are related to the frame rate of said displaying means.

9. The ultrasonic diagnostic imaging system of claim 8, wherein said displaying means comprises means for displaying increases in fluid velocity to visually correspond to actual rate of occurrence, and decreases in fluid velocity to visually correspond to a rate of decline at a time constant increased in relation to actual rate of occurrence and visually invariant in the presence of changes in the frame rate of said displaying means.

10. An ultrasonic diagnostic imaging system for imaging conditions of fluid flow within the body comprising:
means for acquiring echo information from structure within the body, including Doppler information signals from fluid moving relative to said acquiring means; .
means for processing said Doppler information signals to produce fluid velocity signals as a function of location within the body in which time sequences of successive fluid velocity signals related to a given location indicate increases or decreases in fluid velocity at said location in relation to their rate of occurrence;
user adjustable means for determining the rate at which frames of fluid velocity information are displayed;
user selectable means for selecting one of a plurality of time constants for the display of decreases in fluid velocity;
means, responsive to said user adjustable means and said user selectable means, for altering successive fluid velocity signals indicating fluid velocity decrease to exhibit a rate of decay determined by said selected time constant, said altering being further related to the rate at which frames of fluid velocity information are displayed; and
means, responsive to said altering means, for displaying fluid velocity information.

11. The ultrasonic diagnostic imaging system of claim 10, wherein said altering means further includes means for selectively altering successive fluid velocity signals indicating fluid velocity increase to exhibit said increase at its rate of occurrence.

12. An ultrasonic diagnostic imaging system for imaging conditions of fluid flow within the body comprising:
means for acquiring echo information from structure within the body, including Doppler information signals from fluid moving relative to said acquiring means;
means for processing said Doppler information signals to produce fluid velocity signals as a function of location within the body, wherein successive fluid velocity signals related to a given location indicate increases or decreases in fluid velocity at said location occurring over time;

means, responsive to successive fluid velocity signals, for producing output signal sequences in which increases in fluid velocity are represented at their actual rate of change and in which decreases in fluid velocity are represented at less than their actual rate of change, said processing means comprising means for processing fluid velocity signals $x_n$ to produce output signals $y_n$ in accordance with the expression if $x_n > y_{n-1}$, then $y_n = x_n$;

if $x_n < y_{n-1}$, then $y_n = (1-k)x_n + ky_{n-1}$, where n is a function of time and the weighting factor k is greater than zero and less than one; and means, responsive to said output signal sequences, for displaying fluid velocity information.

13. The ultrasonic diagnostic imaging system of claim 12, wherein said displaying means displays frames of fluid velocity information at a variable frame rate, and wherein the weighting factor k is determined by the expression $$k = e^{-1/[(FR)(t_p)]},$$

where FR is the frame rate and $t_p$ is a persistence time constant.

* * * * *